United States Patent [19]
de Cordova

[11] Patent Number: 6,088,836
[45] Date of Patent: Jul. 18, 2000

[54] AUDIO/VISUAL SENSORY INHIBITOR

[76] Inventor: James H. de Cordova, 17 Brooks Ave., #A, Venice Beach, Calif. 90291

[21] Appl. No.: 09/159,356

[22] Filed: Sep. 23, 1998

[51] Int. Cl.[7] .................................................. A42B 1/00

[52] U.S. Cl. ............................ 2/171; 2/15; 2/173; 2/206; 2/209.3

[58] Field of Search .............................. 2/9, 15, 171, 173, 2/174, 206, 209.3, 209.4, 452, DIG. 11; 128/857, 858; 5/636, 640

[56] References Cited

U.S. PATENT DOCUMENTS

| 3,541,608 | 11/1970 | Otwell | 2/15 |
| 5,425,380 | 6/1995 | Hudson et al. | 2/15 |

*Primary Examiner*—Bibhu Mohanty
*Attorney, Agent, or Firm*—W. D. English, III

[57] ABSTRACT

A meditation and sleep enhancing device having a light occlusion portion attached to a head rest portion and a chin-strap extending therefrom. When in use by an individual, the sleep enhancing device acts both as a light and sound suppression device as well as providing a comfortable pillow and neck support. When not in use, the chin strap may be used as a handle to easily transport the device.

16 Claims, 3 Drawing Sheets

AUDIO/VISUAL SENSORY INHIBITOR

FIELD OF THE INVENTION

The invention relates to an audio and visual sensory inhibitor and more specifically to a sleep enhancing apparatus in the form of a combined system for occluding light and sound and for providing a head rest during sleep in a secure yet comfortable manner while traveling in a public conveyance such as a train, air plane, boat, or bus.

BACKGROUND OF THE INVENTION

Conventionally, as illustrated in U.S. Pat. Nos. 4,872,217 and 5,435,006 to Kitayama, eye masks have been affixed to a wearer through the use of elastic bands. Besides the lack of auditory occlusion and head support, the use of elastic bands can cause pressure headaches and does not provide adequate stability to maintain an eyepiece over the eyes of the user.

U.S. Pat. No. 5,343,561, to Adamo, basically discloses an eye mask with a method of attachment around the ears. Although Adamo's device may occlude sound, the elastic means of attachment around the ears is very impractical and uncomfortable. This device also discloses a separate "U" shaped device to be worn around the neck to provide neck support. Having two separate units that are not flexible makes storage and transportation of the device difficult and cumbersome.

U.S. Pat. No. 5,224,495, to Robinson, discloses a box shaped device that the user may wear over his head. However, the device has slits on the sides allowing light to penetrate and thereby somewhat defeating the purpose of the invention. In addition, ear plug members are inserted into the user's ears to occlude sound, thereby making the invention uncomfortable and possibly unsanitary.

In general, prior art sleep aid devices do not function adequately, are uncomfortable to use, and are not easily transportable. Therefore, there remains a long standing and continuing need for an advance in the art beyond the existing sleep enhancing devices that is simpler and more comfortable in both design and use, is more economical and efficient in its construction and use, and can be readily, conveniently, and compactly transported.

OBJECTS OF THE INVENTION

It is a primary object of the invention to eliminate auditory and visual sensory stimulation to provide a user with Rapid Eye Movement (REM) sleep, and undisturbed meditation in the alpha, delta, and theta states, and in general a state of optimum relaxation.

It is another object of the invention to occlude all light from disturbing a user's sleep.

It is another object of the invention to minimize auditory disturbance while a user is in a state of quiet meditation or sleep.

Yet another object of the invention is to provide a user with maximum head support and comfort to allow optimum meditation or REM sleep.

Another object of the invention is to allow a secure yet comfortable cushioned pillow like head wrap for leaning against a wall or shoulder of another while in a sitting or lying position.

Another object of the invention is to provide a sleep enhancing device that is easy to stare for transport.

Yet another object of the invention is to provide a sleep enhancing device that is economical and simple to construct.

Yet another object of the invention is to convert the sleep enhancing device into a travel pillow by inserting the eyepiece and strap into a pocket of the head wrap.

Yet another object of the invention is to convert the sleep enhancing device into a hand muff by inserting the eyepiece and strap into a pocket of the head wrap.

Such stated objects and advantages of the invention are only examples and should not be construed as limiting this invention. Other objects and advantages of the invention herein will become more apparent from a description of the invention and the claims that follow.

DETAILED DESCRIPTION OF THE INVENTION

Figure 1:
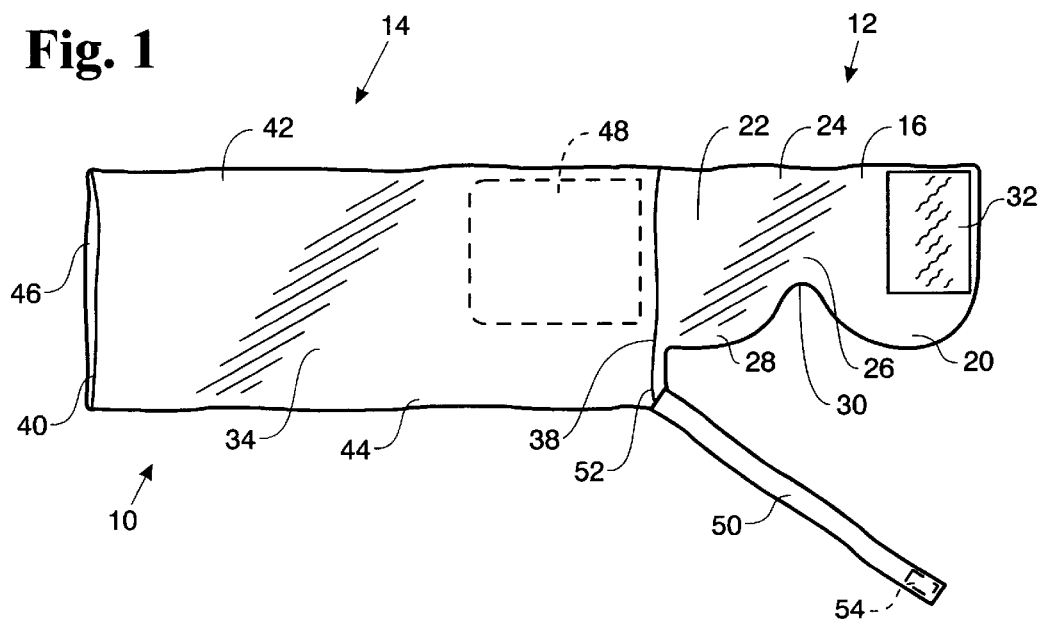
FIG. 1 is an elevational view of the unfolded/unrolled outside layer of the sleep enhancing apparatus.
Figure 2:
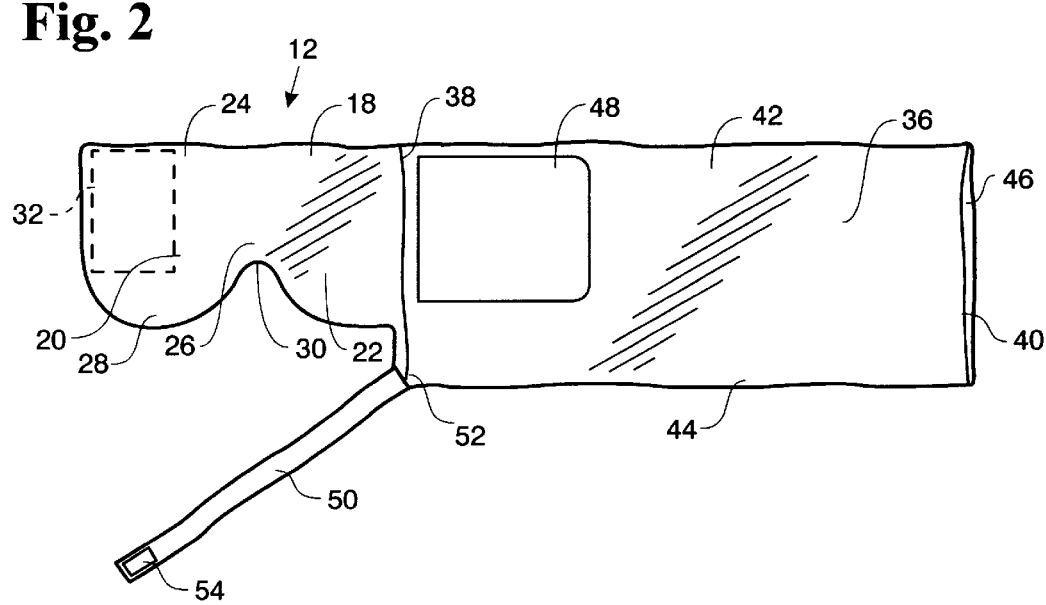
FIG. 2 is an elevational view of the unfolded/unrolled inside layer of the sleep enhancing apparatus.

Referring now to FIGS. 1 and 2, an embodiment of a traveler's sleep enhancing apparatus 10 is depicted. Apparatus 10 has an eye cover, light occlusion portion 12, that 12 is connected to a wrap around, noise inhibiting ear cover and head contact unit 14.

Eye cover 12 has an outer surface 16 and an inner surface 18. Eye cover 12 is constructed of an opaque and soft material, such that light is occluded yet it is still comfortable to wear. Eye cover 12 has a left eye cover 20, a right eye cover 22, a top area 24, and a middle nose area 26. Left eye cover 20 has an attaching means 32 disposed thereon. Attaching means 32 may be any conventional attaching mechanism such as, but not limited to, a hook and loop fastener such as Velcro®. When apparatus 10 is wrapped around a traveler's head to function as a wrap around pillow, attaching means 32 removably connects to a second attacking means 33 located on a distal end of head contact unit 14. A bottom area 28 of eye cover 12 is shaped to adapt to a user's face, wherein the distance between top area 24 and bottom area 28 is shorter at middle area 26 than at bottom area 28 of left and right eye covers 20 and 22. Thereby, a ridge of a user's nose may be inserted into a basin 30 defined by bottom area 28 at middle area 26. Left eye cover 20 and right eye cover 22 may be cupped or convex to maintain inner surface 18 at an appropriate distance from a user's eyes, in order to accommodate rapid eye movement during sleep.

Figure 5:
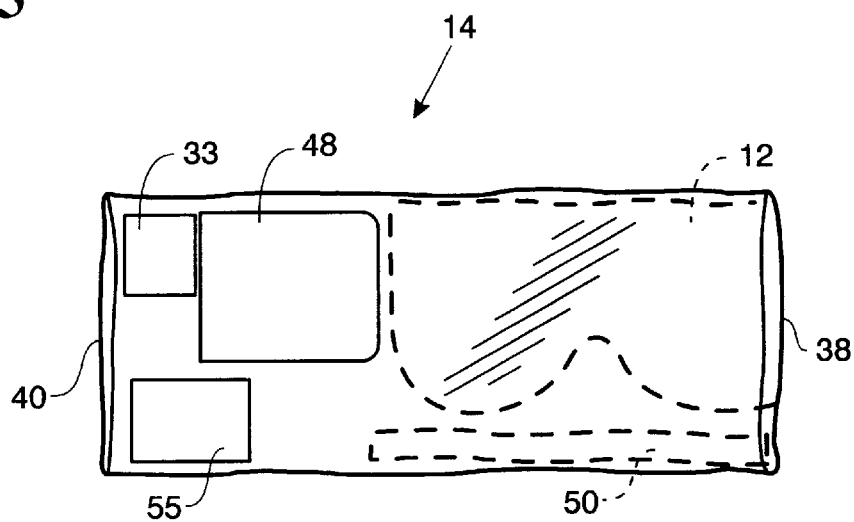
FIG. 5 is another view of FIG. 1 illustrating how the eye cover and chin strap may be folded inside the wrap around pillow, head contact portion, of the invention.
Figure 6:
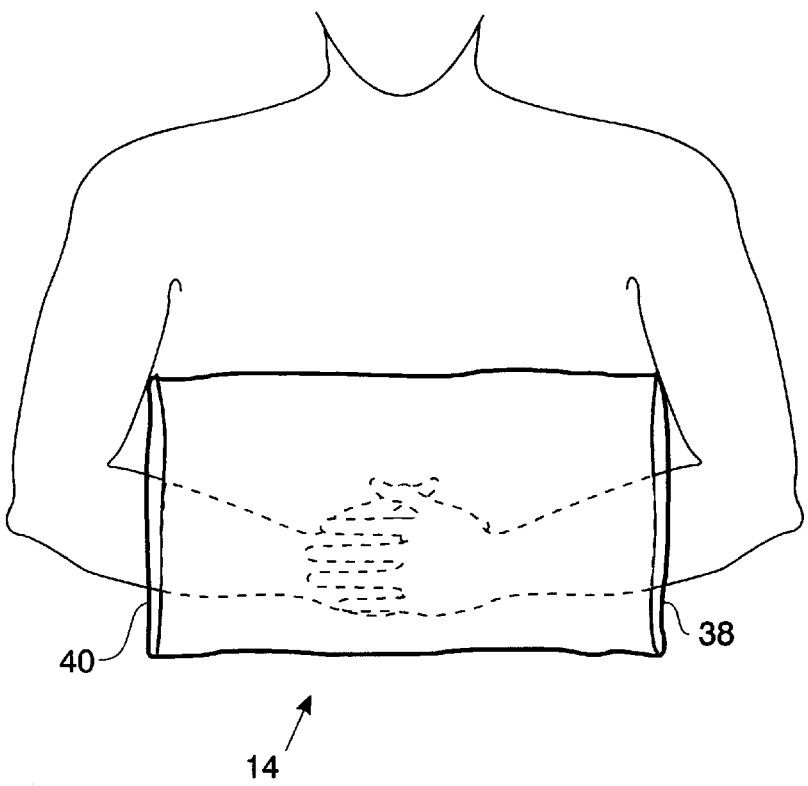
FIG. 6 is another view of FIG. 5 illustrating how the invention may alternately be used as a hand muff to keep hands warm.

Unit 14 has an inner layer 36 and an outer layer 34. Unit 14 has a primary, right edge 28, a secondary, left edge 40, a top edge 42, and a bottom edge 44. Unit 14 is made of a soft and flexible material to provide comfort for the user. A cushioning layer 46 is maintained between inner layer 36 and outer layer 36 to provide a comfortable head rest, pillow for a traveller 70. Cushioning layer 46 may be any comfortable element, such as, but not limited to, fleece, cotton, air, or any combination thereof Cushioning layer 46 may also contain additional materials of predetermined density to occlude sounds beyond a predetermined decibel level. Outer layer 44 has disposed thereon a pocket 48 for storing items or devices, such as, but not limited to, an alarm clock may be stored in pocket 48. A cavity 47 may be defined by cushioning layer 46 and outer layer 34, wherein light occlusion portion 12 and an attaching strap 50 may be inserted when the invention is not in use as and eye and ear cover as well as a pillow. When not in use as an eye and ear cover and pillow, the invention may also be used as a hand muff, hand warmer, as indicated in FIGS. 5 and 6 by inserting one's hands at either end 38 and 40 of head contact unit 14.

Figure 3:
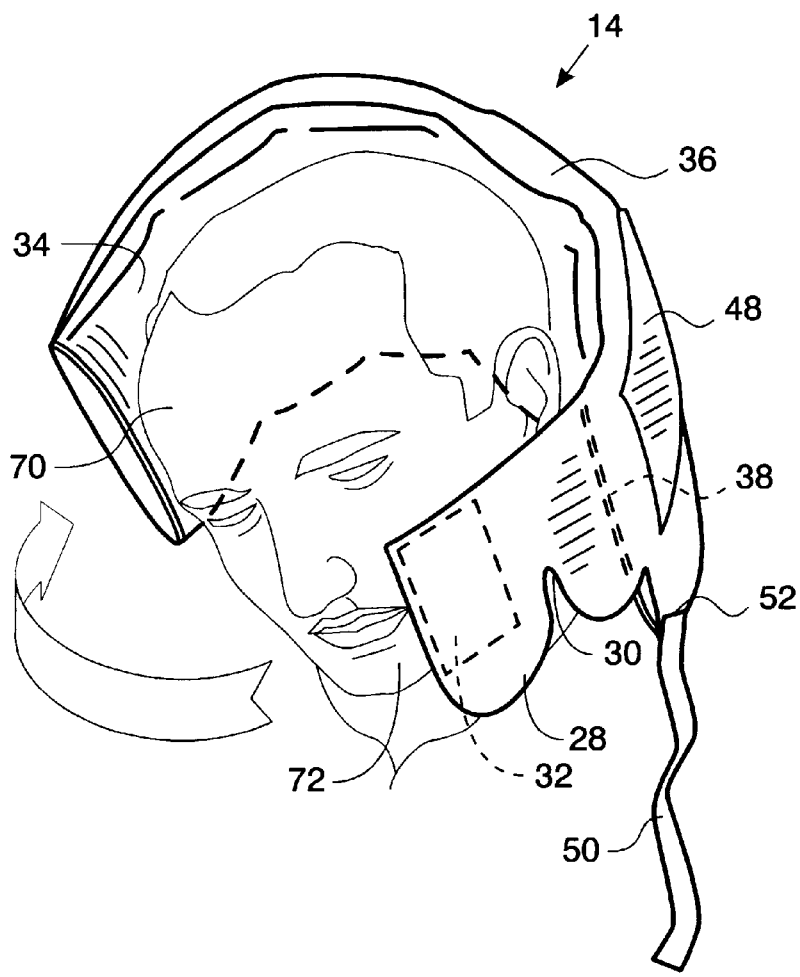
FIG. 3 is a perspective view of the sleep enhancing apparatus being mounted and wrapped around the head of a traveler.
Figure 4:
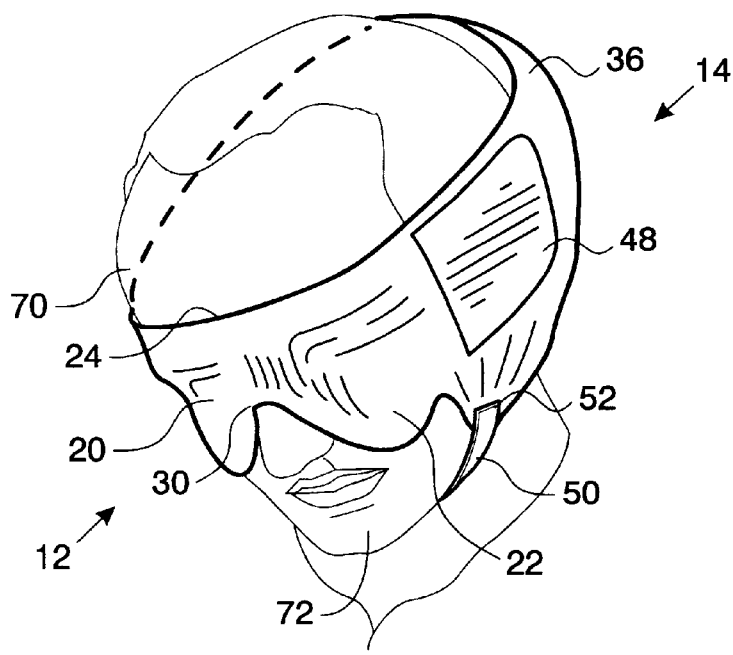
FIG. 4 is a perspective view of the sleep enhancing apparatus worn by a user.

Referring to FIGS. 3 and 4, an optional attaching strap 50 is extends from a junction 52. Junction 52 is formed at an attaching point of primary, right edge 38 of unit 14 and right eye cover 22 of portion 12. Strap 50 has a removable binding means 54, which may be, but is not limited to, a hook and loop fastener. Binding means 54 is disposed at an end of strap 50 opposing junction 52. Binding means 54 removably attaches to left edge 40 of unit 14 when apparatus 10 is in use, and fits under a chin 72 of traveler 70. A binding region 55 is provided on left edge 40 of unit 14 to receive binding means 54.

While the above description contains many specificities, these should not be construed as limitations on the scope of the invention, but rather as an exemplification of one preferred embodiment thereof. Many other variations are possible without departing from the essential spirit of this invention. Accordingly, the scope of the invention should be determined not by the embodiment illustrated, but by the appended claims and their legal equivalents.

What is claimed is:

1. A traveler's wrap around pillow, sleep enhancing device, comprising: a light occlusion, eye cover portion attached to an adjustable noise inhibiting wrap around pillow, head rest portion, wherein a traveler's eyes are, may be covered by said light occlusion portion, and the head and ears of the traveler may be encompassed by said head rest portion.

2. The sleep enhancing device of claim 1, wherein said light occlusion portion has a right eye cover and a left eye cover, and said head rest portion has a right edge and a left edge;

said right eye cover being connected to said right edge;

said left eye cover of said occlusion portion has an attaching means disposed thereon;

whereby said attaching means may be removably connected with said left edge at varying points thereon, allowing said apparatus to be adjustable to varying sizes of heads.

3. The sleep enhancing device of claim 2, wherein a strap is connected to a junction between said right eye cover and said right edge;

said strap having a binding means at an end furthest from said junction;

said strap adapted to traverse under a chin of a user, and said binding means adapted to fixedly, yet removably attach to varying points on said left edge.

4. The sleep enhancing device of claim 2, wherein a pocket is attached to said head rest portion.

5. The sleep enhancing device of claim 4, wherein said strap may function as a carrying handle when said device is in transit.

6. The sleep enhancing device of claim 1, wherein said light occlusion potion has a basin portion to receive a nose of a user.

7. The sleep enhancing device of claim 1, wherein said light occlusion portion is made of an opaque material.

8. The sleep enhancing device of claim 1, wherein said light occlusion material is constructed of a material selected from the group consisting of velvet, satin, cotton, denim, silk, and plastic.

9. The sleep enhancing device of claim 1, wherein said head rest portion is constructed of a material selected from the group consisting of velvet, satin, cotton, denim, silk, and plastic.

10. The sleep enhancing device of claim 1, wherein said head rest portion has a first layer of material and a second layer of material.

11. The sleep enhancing device of claim 10, wherein said first layer and said second layer enclose a material that impedes sounds.

12. The sleep enhancing device of claim 11, wherein said material is selected from the group consisting of air, foam, wool, and cotton.

13. The sleep enhancing device of claim 1, wherein said head rest portion is elastically stretchable.

14. The sleep enhancing device of claim 1, wherein said head rest portion may be used without deployment of said light occlusion portion.

15. A sleep enhancing device, comprising:

a light occlusion portion having a right eye cover and a left eye cover, said left eye cover having an attaching means disposed thereon;

a head rest portion having a right edge and a left edge;

said right eye cover of said occlusion portion attaching to said right edge of said head rest portion, and having a strap extending therefrom, said strap having a binding means at an end distal to said right eye cover and right edge;

said head rest portion adapted to encompass the head of a user to position said light occlusion portion over a pair of eyes of the user, said attaching means of said left eye cover of said occlusion portion removable attaching to said left edge of said head rest portion, and said binding means of said strap adapted to traverse a chin of the user and removably bind to said left edge.

16. A head rest of multiple adaptibility, comprising:

an eye occlusion portion having a right eye cover and a left eye cover, said left eye cover having an attaching means disposed thereon;

a head rest portion having a right edge and a left edge;

said right eye cover of said occlusion portion attaching to said right edge of said head rest portion, and extending therefrom, a strap having a binding means at an end distal to said right eye cover and right edge;

said head rest portion adapted to encompass the head of a user to position said light occlusion portion over a pair of eyes of said user, said attaching means of said left eye cover of said occlusion portion removably attaching to said left edge of said head rest portion, and said binding means of said strap adapted to traverse a chin of the user and removably bind to said left edge of said head rest portion.

* * * * *